US008940864B2

(12) United States Patent
Debnath et al.

(10) Patent No.: US 8,940,864 B2
(45) Date of Patent: Jan. 27, 2015

(54) STABILIZED THERAPEUTIC SMALL HELICAL ANTIVIRAL PEPTIDES

(75) Inventors: Asim Kumar Debnath, Fort Lee, NJ (US); Hongtao Zhang, Mount Vernon, NY (US); Qian Zhao, Rego Park, NY (US)

(73) Assignee: New York Blood Center, Inc., New York, NY (US)

( * ) Notice: Subject to any disclaimer, the term of this patent is extended or adjusted under 35 U.S.C. 154(b) by 1498 days.

(21) Appl. No.: 12/438,414

(22) PCT Filed: Oct. 2, 2007

(86) PCT No.: PCT/US2007/021156

§ 371 (c)(1), (2), (4) Date: Feb. 23, 2009

(87) PCT Pub. No.: WO2008/045238

PCT Pub. Date: Apr. 17, 2008

(65) Prior Publication Data

US 2010/0130430 A1 May 27, 2010

Related U.S. Application Data

(60) Provisional application No. 60/849,551, filed on Oct. 5, 2006.

(51) Int. Cl.

*C07K 7/08* (2006.01)
*A61K 38/00* (2006.01)
*A61K 38/04* (2006.01)
*C07K 7/00* (2006.01)

(52) U.S. Cl.

CPC .. *C07K 7/08* (2013.01); *A61K 38/00* (2013.01)
USPC ............. 530/326; 530/327; 530/328; 514/1.1

(58) Field of Classification Search

None
See application file for complete search history.

(56) References Cited

U.S. PATENT DOCUMENTS

| | | | | |
|---|---|---|---|---|
| 6,187,548 | B1 * | 2/2001 | Akerstrom et al. | 435/7.2 |
| 6,239,270 | B1 * | 5/2001 | Akerstrom et al. | 536/24.3 |
| 6,653,102 | B2 * | 11/2003 | Roch et al. | 435/69.1 |
| 6,790,950 | B2 * | 9/2004 | Lowery et al. | 536/23.7 |
| 7,723,469 | B2 | 5/2010 | Walensky et al. | |
| 7,763,262 | B2 * | 7/2010 | Lowery et al. | 424/255.1 |
| 2006/0008848 | A1 | 1/2006 | Verdine et al. | |
| 2009/0149630 | A1 | 6/2009 | Walensky et al. | |
| 2009/0176964 | A1 | 7/2009 | Walensky et al. | |
| 2010/0151483 | A1 * | 6/2010 | Hornbeck et al. | 435/7.1 |
| 2010/0159477 | A1 * | 6/2010 | Hornbeck et al. | 435/7.4 |
| 2010/0168388 | A1 | 7/2010 | Bernal et al. | |
| 2010/0267608 | A1 * | 10/2010 | Das Gupta et al. | 514/1.1 |
| 2010/0286057 | A1 | 11/2010 | Walensky et al. | |
| 2011/0218155 | A1 | 9/2011 | Walensky et al. | |
| 2011/0318352 | A1 | 12/2011 | Walensky et al. | |

FOREIGN PATENT DOCUMENTS

| | | | | |
|---|---|---|---|---|
| WO | WO 0061724 | * 10/2000 | A61K 38/00 |
| WO | 2005/044839 A2 | 5/2005 | |

OTHER PUBLICATIONS

Sticht et al. A peptide inhibitor of HIV-I assembly in vitro. Nature Structural & Molecular Biology. Aug. 2005, vol. 12, No. 8, pp. 671-677 (cited as "A" reference in r/t PCT Search Report).*
Ternois et al. The HIV-I capsid protein C-terminal domain in complex with a virus assembly inhibitor. Nature Structural & Molecular Biologyo Aug. 2005. vol. 12. No. 8, pp. 678-682. (cited as "A" reference in r/t PCT Search Report).*
Ternois et al. The HIV-1 capsid protein C-terminal domain in complex with a virus assembly inhibitor. Nature Structural & Molecular Biology (2005), 12(8),678-682 (abstract provided, available online).*
Sticht et al. A peptide inhibitor of HIV-1 assembly in vitro. Nature Structural & Molecular Biology (2005), 12(8),671-677 (abstract provided, available online).*
Shoelson et al. YMXM motifs of IRS-1 define substrate specificity of the insulin receptor kinase. Proceedings of the National Academy of Sciences of the United States of America (1992), 89(6), 2027-31 (abstract provided, available online).*
Sticht, J. et al. A peptide inhibitor of HIV-1 assembly in vitro. Nat. Struct. Mol Biol. 12, 671-677 (2005) (cited in application).*
Ternois, F., Sticht, J., Duquerroy, S., Krausslich, H. G., & Rey, F. A. The HIV-1 capsid protein C-terminal domain in complex with a virus assembly inhibitor. Nat. Struct. Mol Biol. 12, 678-682 (2005) (cited in application).*
Schafmeister et al., J. Am. Chem. Soc. 122:5891-5892 (2000) (cited by Applicant also).*
Walenski et al., Science 305:1466-1470 (2004) (cited by Applicant also).*
http://en.wikipedia.org/wiki/Capsid (Last Updated: Jul. 25, 2014).*
Sticht et al., A peptide inhibitor of HIV-1 assembly in vitro, Nature Structural & Molecular Biology, Aug. 2005, vol. 12, No. 8, pp. 671,677.
Ternois et al., "The HIV-1 capsid protein C-terminal domain in complex with a virus assembly inhibitor", Nature Structural & Molecular Biology, Aug. 2005, vol. 12, No. 8, pp. 678-682.
Abdurahman, S., Hoglund, S., Goobar-Larsson, L., & Vahlne, A. Selected ammo acid substitutions in the C-terminal region of human immunodeficiency virus type 1 capsid protein affect virus assembly and release. J Gen Virol 85, 2903-2913 (2004).

(Continued)

*Primary Examiner* — Maury Audet
(74) *Attorney, Agent, or Firm* — K&L Gates LLP; Louis C. Cullman; Michelle Glasky Bergman

(57) ABSTRACT

Provided are constrained peptides that inhibit HIV assembly. Pharmaceutical compositions comprising the above peptides are also provided. Additionally provided are methods of inhibiting replication of a capsid-containing virus in a cell. Also provided are methods of treating a mammal infected with a capsid-containing virus. Further provided are methods of treating a mammal at risk for infection with a capsid-containing virus. Methods of making the above peptides are additionally provided, as are uses of the above peptides and pharmaceutical compositions.

34 Claims, 6 Drawing Sheets

(56) References Cited

OTHER PUBLICATIONS

Chien, A.I., Liao, W.H., Yang, D.M., & Wang, CT. A domain directly C-terminal to the major homology region of human immunodeficiency type 1 capsid protein plays a crucial role in directing both virus assembly and incorporation of Gag-Pol. Virology. 348, 84-95 (2006).

Chu, H.H., Chang, Y.F., & Wang, CT. Mutations in the alpha-helix Directly C-terminal to the Major Homology Region of Human Immunodeficiency Virus Type 1 Capsid Protein Disrupt Gag Multimerization and Markedly Impair Virus Particle Production. J Biomed. Sci. 13, 645-56 (2006).

Derdeyn, CA. et al. J Virol. 74, 8358 (2000).

Derdowski, A., Ding, L., & Spearman, P. A Novel Pluorescence Resonance Energy Transfer Assay Demonstrates that the Human Immunodeficiency Virus Type 1 Pr55Gag I Domain Mediates Gag-Gag Interactions. The Journal of Virology 78, 1230-1242 (2004).

Dong, X. et al. AP-3 directs the intracellular trafficking of HIV-I Gag and plays a key role in particle assembly. Cell. 120, 663-674 (2005).

Douglas, CC, Thomas, D., Lanman, J., & Prevelige, P.E., Jr. Investigation of N- terminal domain charged residues on the assembly and stability of HIV-I CA. Biochemistry.43, 10435-10441 (2004).

Forshey, B.M., von Schwedler, U., Sundquist, W.I., & Aiken, C Formation of a human immunodeficiency virus type 1 core of optimal stability is crucial for viral replication. J Virol. 76, 5667-5677 (2002).

Freed, E.O. HIV-I gag proteins: diverse functions in the virus life cycle. Virology. 251, 1-15 (1998).

Garzon, M.T. et al. The dimerization domain of the HIV-I capsid protein binds a capsid protein-derived peptide: a biophysical characterization. Protein Sci 13, 1512-1523 (2004).

Ganser-Pornillos, B.K., von Schwedler, U.K., Stray, K.M., Aiken, C, & Sundquist, W.I. Assembly properties of the human immunodeficiency virus type 1 CA protein. J Virol 78, 2545- 2552 (2004).

Gottlinger, H.G. The HIV-I assembly machine. AIDS Suppl 5, S13-S20 (2001).

Grigorov, B., Arcanger, F., Roingeard, P., Darlix, J.L., & Muriaux, D. Assembly of infectious HPV-I in human epithelial and T-lymphoblastic cell lines. J Mol Biol. 359, 848-862 (2006).

Gross, I. et al. J. Virol 72, 4798 (1998).

Guo, X. et al. The R362A mutation at the C-terminus of CA inhibits packaging of human immunodeficiency virus type 1 RNA. Virology 343, 190-200 (2005).

Hoglund, S. et al. Tripeptide interference with human immunodeficiency virus type 1 morphogenesis. Antimicrob. Agents Chemother. 46, 3597-3605 (2005).

Huseby, D., Barklis, R.L., Alfadhli, A., & Barklis, E. Assembly of human immunodeficiency virus precursor gag proteins. J Biol. Chem. 280, 17664-17670 (2005).

Jiang, S., et al. Journal of Experimental Medicine 174, 1557-1563 (1991).

Jiang, S. et al. Antimicrobial Agents and Chemotherapy 48, 4349-4359 (2004).

Joshi, A., Nagashima, K., & Freed, E.O. Mutation of dileucine-like motifs in the human immunodeficiency virus type 1 capsid disrupts virus assembly, gag-gag interactions, gag-membrane binding, and virion maturation. J Virol. 80, 7939-7951 (2006).

Kieber-Emmons et al. Curr. Opin. Biotechnol. 8, 435-441 (1997).

Kramer, B. et al. HIV interaction with endosomes in macrophages and dendritic cells. Blood Cells Mol Dis. 35, 136-142 (2005).

Leduc, A.M. et al. Helix-stabilized cyclic peptides as selective inhibitors of steroid receptor-coactivator interactions. Proc Natl Acad Sci U S A. 100, 11273-11278 (2003).

Li, F. et al. PA-457: a potent HIV inhibitor that disrupts core condensation by targeting a late step in Gag processing. Proc Natl Acad Sci U S A 100, 13555-13560 (2003).

Morikawa, Y. HIV capsid assembly. Curr HIV Res 1, 1-14 (2003).

Lundberg, M. et al. Biochem. Biophys. Res. Commun., 291, 367 (2002).

Niedrig, M. et al. Inhibition of infectious human immunodeficiency virus type 1 particle formation by Gag protein-derived peptides. J Gen Virol 75 ( Pt 6), 1469-1474 (1994).

Nydegger, S., Foti, M., Derdowski, A., Spearman, P., & Thali, M. HIV-I egress is gated through late endosomal membranes. Traffic. 4, 902-910 (2003).

Ono, A. & Freed, E.O. Cell-type-dependent targeting of human immunodeficiency virus type 1 assembly to the plasma membrane and the multivesicular body. J Virol. 78, 1552-1563 (2004).

Pelchen-Matthews, A., Kramer, B., & Marsh, M. Infectious HIV-I assembles in late endosomes in primary macrophages. J. Cell Biol. 162, 443-455 (2003).

Phelan, J.C., Skelton, N.J., Braisted, A.C., & McDowell, R.S. A General Method for Constraining Short Peptides to an a-Helical Conformation. J. Am. Chem. Soc. 119, 455-460 (1997).

Qiu, W. et al. Tetrahedron, 56, 2577 (2000).

Richard, JP et al. J. Biol. Chem., 278, 585 (2003).

Ripka et al. Curr. Opin. Chem. Biol. 2, 441-452 (1998).

Sakalian, M. et al. 3-O-(3',3'-dimethysuccinyl) betulinic acid inhibits maturation of the human immunodeficiency virus type 1 Gap precursor assembled in vitro. J Virol 80:5716-5722 (2006).

Sanderson. Med. Res. Rev. 19, 179-197 (1999).

Schafrneister, C.E., Po ,J., & Verdine, G.L. An All-Hydrocarbon Cross-Linking System for Enhancing the Helicity and Metabolic Stability of Peptides. J. Am. Chem. Soc. 122, 5891-5892 (2000).

Sherer, N.M. et al. Visualization of retroviral replication in living cells reveals budding into multivesicular bodies. Traffic. 4, 785-801 (2003).

Tang, C. et al. Antiviral inhibition of the HTV-I capsid protein. J Mol Biol. 327, 1013-1020 (2003).

Wang, D., Liao, W., & Arora, P.S. Enhanced Metabolic Stability and Protein-Binding Properties of Artificial Helices Derived from a Hydrogen-Bond Surrogate: Application to Bcl-xL. Angewandte Chemie International Edition 44, 6525-6529 (2005).

Walensky, L.D. et al. Activation of Apoptosis in Vivo by a Hydrocarbon-Stapled BH3 Helix. Science 305, 1466-1470 (2004).

Yang, B., Lic, D., & Huang, Z. Synthesis and helical structure of lactam bridged BH3 peptides derived from pro-apoptotic Bcl-2 family proteins. Bioorganic & Medicinal Chemistry Letters 14, 1403-1406 (2004).

* cited by examiner

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial
<220> FEATURE:
<223> OTHER INFORMATION: Synthetic peptide

<400> SEQUENCE: 1

Ile Thr Phe Glu Asp Leu Leu Asp Tyr Tyr Gly Pro
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T

<400> SEQUENCE: 2

Xaa Xaa Xaa Xaa Xaa Xaa Xaa Xaa Xaa Xaa
1               5                   10


<210> SEQ ID NO 3
<211> LENGTH: 10
<212> TYPE: PRT
<213> ORGANISM: Artificial Sequence
```

<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I or V
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (3)..(3)
<223> OTHER INFORMATION: X=F, W or Y
<220> FEATURE:
<221> NAME/KEY: VARIANT
<222> LOCATION: (4)..(4)
<223> OTHER INFORMATION: X=E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (7)..(7)
<223> OTHER INFORMATION: X=L, D or T
<220> FEATURE:
<221> NAME/KEY: VARIANT
<222> LOCATION: (8)..(8)
<223> OTHER INFORMATION: X=D, A or S
<220> FEATURE:
<221> NAME/KEY: VARIANT
<222> LOCATION: (9)..(9)
<223> OTHER INFORMATION: X=Y or F
<220> FEATURE:
<221> NAME/KEY: VARIANT
<222> LOCATION: (10)..(10)
<223> OTHER INFORMATION: X=Y or M

<400> SEQUENCE: 3

```
Xaa Xaa Xaa Xaa Xaa Leu Xaa Xaa Xaa Xaa
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y M or W -continued
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K

<400> SEQUENCE: 4

Xaa Xaa Xaa Xaa Xaa Xaa Xaa Xaa Xaa Xaa Xaa
1 5 10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L, or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K
<220> FEATURE:
<221> NAME/KEY: VARIANT
<222> LOCATION: (12)..(12)
<223> OTHER INFORMATION: X=P, M, R or K

<400> SEQUENCE: 5

-continued

Xaa Xaa Xaa Xaa Xaa Xaa Xaa Xaa Xaa Xaa Xaa Xaa
1 5 10

<210> SEQ ID NO 6
<211> LENGTH: 12
<212> TYPE: PRT
<213> ORGANISM: Artificial
<220> FEATURE:
<223> OTHER INFORMATION: Stapled peptide NYAD-1 based on SEQ ID NO:1
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 6

Ile Thr Phe Xaa Asp Leu Leu Xaa Tyr Tyr Gly Pro
1 5 10

<210> SEQ ID NO 7
<211> LENGTH: 15
<212> TYPE: PRT
<213> ORGANISM: Artificial
<220> FEATURE:
<223> OTHER INFORMATION: Stapled peptide NYAD-13 based on SEQ ID NO:1
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 7

Ile Thr Phe Xaa Asp Leu Leu Xaa Tyr Tyr Gly Pro Lys Lys Lys
1 5 10 15

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT -continued

```
<222> LOCATION: (7)..(7)
<223> OTHER INFORMATION: X=L, D, T, F, I, V, Y M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T

<400> SEQUENCE: 8

Xaa Xaa Xaa Xaa Xaa Xaa Xaa Xaa Xaa Xaa Gly
1               5                   10


<210> SEQ ID NO 9
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L, or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K

<400> SEQUENCE: 9

Xaa Xaa Xaa Xaa Xaa Xaa Xaa Xaa Xaa Xaa Xaa Pro
1               5                   10


<210> SEQ ID NO 10
```

-continued

<211> LENGTH: 10
<212> TYPE: PRT
<213> ORGANISM: Human immunodeficiency virus type 1
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=S-a-2-(4'-pentenyl)alanine
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=S-a-2-(4'-pentenyl)alanine
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T

<400> SEQUENCE: 10

```
Xaa Xaa Xaa Xaa Xaa Xaa Xaa Xaa Xaa Xaa
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)

```
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=S-a-2-(4'-pentenyl)alanine
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=S-a-2-(4'-pentenyl)alanine

<400> SEQUENCE: 11

Xaa Xaa Xaa Xaa Xaa Xaa Xaa Xaa Xaa Xaa Xaa
1               5                   10


<210> SEQ ID NO 12
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X=I, L, or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=S-a-2-(4'-pentenyl)alanine
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K
<220> FEATURE:
```

-continued

<221> NAME/KEY: VARIANT
<222> LOCATION: (12)..(12)
<223> OTHER INFORMATION: X=S-a-2-(4'-pentenyl)alanine

<400> SEQUENCE: 12

Xaa Xaa Xaa Xaa Xaa Xaa Xaa Xaa Xaa Xaa Xaa Xaa
1 5 10

STABILIZED THERAPEUTIC SMALL HELICAL ANTIVIRAL PEPTIDES

CROSS REFERENCE TO RELATED APPLICATIONS

This application is a U.S.C. 371 of PCT/US2007/021156 filed on Oct. 2, 2007, which claims the benefit of U.S. provisional patent application No. 60/849,551, filed Oct. 5, 2006, the entire disclosure of which is incorporated herein by reference.

BACKGROUND OF THE INVENTION (1) Field of the Invention

The present invention generally relates to treatments for HIV infection. More specifically, the invention provides peptides that inhibit assembly of capsid-containing viruses and methods for using those peptides to treat capsid-containing viruses including HIV.

(2) Description of the Related Art

Assembly is a critical step in the HIV-1 life cycle (Morikawa, 2003; Huseb et al., 2005; Gottliger, 2001; Freed, 1998) and generally thought to occur through the controlled polymerization of the gag polyprotein, which is transported to the plasma membrane where the assembly takes place and the virus particles are formed and bud out as spherical immature non-infectious particles. Recent data indicate that gag polyprotein can also accumulate and assemble into viral particles in the late endosomes, often called multivesicular bodies (MVB), especially in macrophages (Pelchen-Matthews et al., 2003; Grigorov et al., 2006; Kramer et al., 2005; Nydegger et al., 2003; Ono and Freed, 2004; Sherer et al., 2003). The virus particles are released when MVB fuses with the plasma membrane.

It has recently been shown that a cellular protein, AP-3, directs the intracellular trafficking of gag to the MVB (Dong et al., 2005). Immediately after the budding, the particles undergo a process termed as maturation, which is essential for the virus to become infectious, where the gag polyprotein is sequentially cleaved by the viral protease to matrix (MA), capsid (CA), nucleocapsid (NC) and p6 domains as well as two spacer proteins, SP1 and SP2. This process triggers a dramatic change in morphology of the particles and an electron dense core is formed surrounded by conical capsid. The formation of mature capsid (CA) play critical role in viral infectivity. The mutations in the CA have been shown to have detrimental effects in viral assembly (Abdurahman et al., 2004; Chien et al., 2006; Chu et al., 2006; Douglas et al., 2004; Forshey et al., 2002; Ganser-Pornillos et al., 2004; Guo et al., 2005; Joshi et al., 2006). Therefore, capsid plays important role in viral assembly, which is critical in HIV-1 life cycle and has been considered as potential target for developing new generations of drugs against HIV-1.

The major obstacle in developing drugs against assembly has been the lack of effective screening system although some new assay method has been reported recently (Derdowski et al., 2004). Despite this difficulty, there are reports of identifying peptides or small molecule compounds that disrupt HIV-1 assembly (Niedrig et al., 1994; Hoglund et al., 2002; Garzon et al., 2004; Tang et al., 2003; Sakalian et al., 2006; Li et al., 2003). The first breakthrough in identifying small molecule inhibitors (CAP-1 and CAP-2) of capsid was reported by Summers' group (Tang et al., 2003). Although the affinity ($K_d$) of CAP-1 to N-terminal CA (N-CA) was only ~800 μM the identification was the initiator to search for potential inhibitors against this target. Another potent small molecule inhibitor, PA-457, which targets gag processing has been recently reported (Li et al., 2003). These small molecule inhibitors interfere with maturation of HIV-1. The later compound is currently undergoing Phase II clinical trials.

Recently, a small linear peptide (CAI) has been identified by phage display technique, which inhibits HIV-1 assembly in vitro by targeting the C-terminal CA (C-CA) of capsid (Sticht et al., 2005). Although x-ray crystallographic analysis revealed that CAI forms a helix and binds to a hydrophobic groove formed by helices 1, 2 and 4 of C-CA (Ternois et al., 2005) its conformation in solution has not been reported. The dissociation constant ($K_d$) was estimated to be ~15 μM. CAI was the first compound reported to have inhibition against both immature and mature HIV-1 particles in vitro. However, the major drawback of CAI is that it cannot penetrate cells, thereby, cannot be used as an assembly inhibitor in living cells.

It would be desirable to have an inhibitor of HIV assembly that can penetrate infected cells. The present invention addresses that need.

SUMMARY OF THE INVENTION

The present invention is based on the discovery that α-helical peptides that are anti-viral in vitro but cannot penetrate cells can be made to penetrate cells and be active in vivo if the peptide is stabilized using cross-linking procedures that increase the α-helicity of the peptide in solution.

The present invention is directed to peptides from 10 to 23 amino acids long, wherein two of the amino acids are unnatural amino acids having either R or S stereochemistry at the α-carbon, wherein the α-carbon of the unnatural amino acids comprises a methyl group and an olefinic group, where the two olefinic groups of the unnatural amino acids are on the same side of the α-helix and are joined to form a cross-link between the two unnatural amino acids, wherein the sequence of the amino acids of the peptide comprises (I/L/V)(T/S/A/V/C)(F/I/L/V/M/W)(D/E/S)(D/E)(L/F/I/V/Y/M/W)(L/D/T/F/I/V/Y/M/W)(D/E/A/S)(Y/F/I/L/V/M/W)(Y/F/I/L/V/M/T) (SEQ ID NO:2) or mimetics thereof, wherein the two unnatural amino acids replace two of the amino acids at any positions 3 amino acids apart (i and i+3), 4 amino acids apart (i and i+4) or 7 amino acids apart (i and i+7), and wherein the cross-link between the two unnatural amino acids is a C1-C10 alkyl, alkenyl, alkynyl, $(R1\text{-}K\text{-}R1)_n$; each of which is substituted with a 0-6 R2, wherein R1 is an alkyl, alkenyl or alkynyl;

K is O, S, SO, $SO_2$, CO, CONR4, or

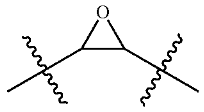

;

R2 is a halo, C1-C10 alkyl, OR3, $N(R3)_2$, SR3, SOR3, $SO_2R3$, $CO_2R3$, R3, a fluorescent moiety or a radioisotope;

R3 is H or a C1-C10 alkyl;

R4 is H, alkyl or a therapeutic agent; and n is an integer from 1-4.

The invention is also directed to pharmaceutical compositions comprising the above-described peptides that can inhibit assembly of a capsid-containing virus, in a pharmaceutically acceptable carrier.

Additionally, the invention is directed to methods of inhibiting replication of a capsid-containing virus in a cell. The methods comprise contacting the cell with the above-described peptides that can inhibit assembly of a capsid-containing virus, in a manner sufficient to inhibit replication of the capsid-containing virus in the cell.

The invention is further directed to methods of treating a mammal infected with a capsid-containing virus. The methods comprise administering the above-described pharmaceutical composition to the mammal in a manner sufficient to treat the mammal.

The present invention is additionally directed to methods of treating a mammal at risk for infection with a capsid-containing virus. The methods comprise administering the above-described pharmaceutical composition to the mammal in a manner sufficient to treat the mammal.

Further, the invention is directed to methods of making any of the above-described peptides. The methods comprise sequentially coupling the amino acids, then joining the two olefinic groups of the unnatural amino acids together using olefin metathesis.

The present invention is also directed to the use any of the above-described peptides that can inhibit assembly of a capsid-containing virus for the manufacture of a medicament for the treatment of a mammal infected with a capsid-containing virus.

Additionally, the present invention is directed to the use any of the above-described peptides that can inhibit assembly of a capsid-containing virus for the manufacture of a medicament for the treatment of a mammal to reduce the risk of the mammal becoming infected with a capsid-containing virus.

Also, the invention is directed to the use of the above-described pharmaceutical compositions for the treatment of a mammal infected with a capsid-containing virus.

The invention is additionally directed to the use of the above-described pharmaceutical compositions for the treatment of a mammal at risk for infection with a capsid-containing virus.

DETAILED DESCRIPTION OF THE INVENTION

Figure 1:
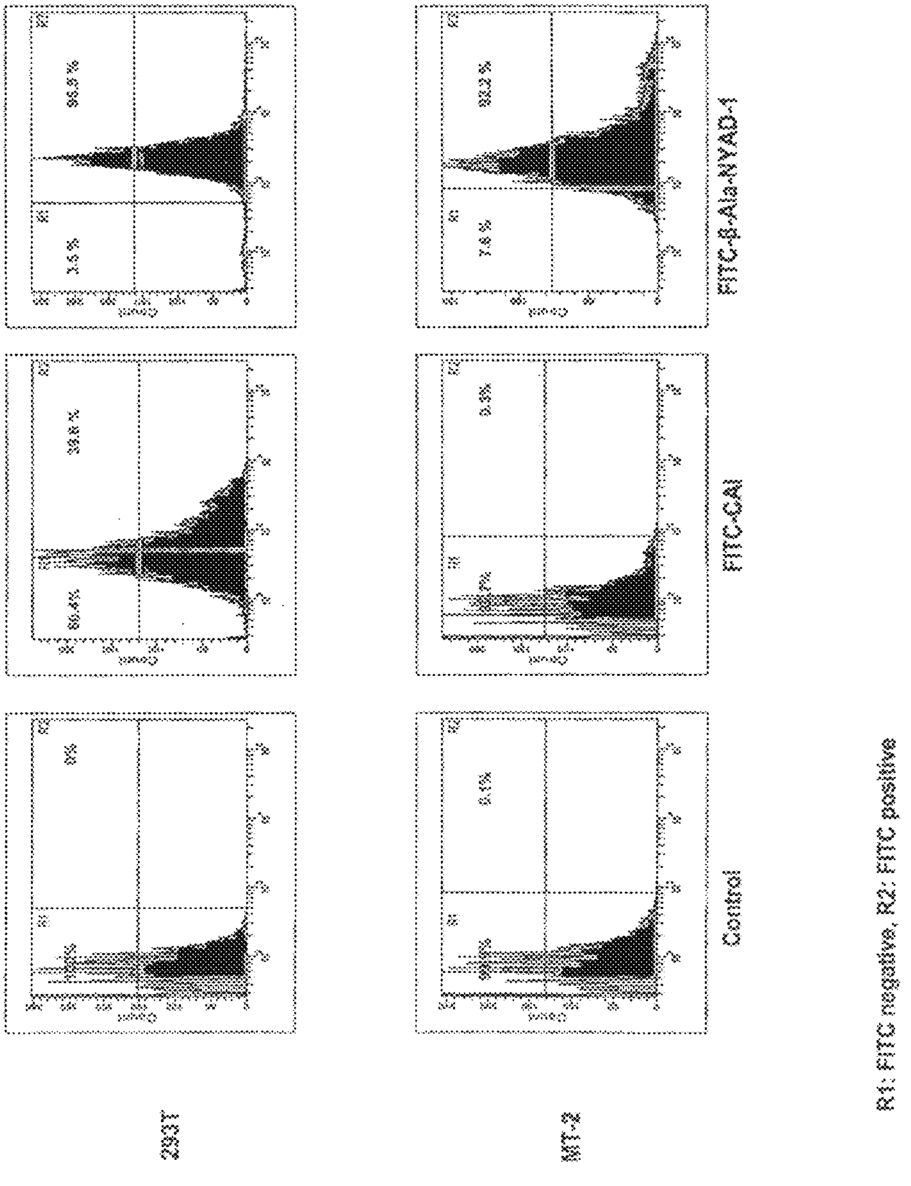
FIG. 1 is graphs of experimental results showing cell penetration and/or association of the linear (SEQ ID NO:1; CA1) and constrained peptides (NYAD-1). The graphs are FACS analyses of 293T and MT2 cells incubated for 4 hours at 37° C. with FITC-conjugated peptides. Cells were washed 3 times with PBS before analysis. Upper panel: Left, FACS analysis of 293T cells without FITC-peptide. Center, FACS analysis of 293T cells with FITC-CAI. Right, FACS analysis of 293T cells with FITC-β-Ala-NYAD-1. Lower panel: Left, FACS analysis of MT-2 cells without FITC-peptide. Center, FACS analysis of MT-2 cells with FITC-CAI. Right, FACS analysis of MT-2 cells with FITC-P-Ala-NYAD-1.

The present invention is directed to peptides from 10 to 23 amino acids long, wherein two of the amino acids are unnatural amino acids having either R or S stereochemistry at the α-carbon, wherein the α-carbon of the unnatural amino acids comprises a methyl group and an olefinic group, where the two olefinic groups of the unnatural amino acids are on the same side of the α-helix and are joined to form a cross-link between the two unnatural amino acids, wherein the sequence of the amino acids of the peptide comprises (I/L/V)(T/S/A/V/C)(F/I/L/V/M/W)(D/E/S)(D/E)(L/F/I/V/Y/M/W)(L/D/T/F/I/V/Y/M/W)(D/E/A/S)(Y/F/I/L/V/M/W)(Y/F/I/L/V/M/T) (SEQ ID NO:2) or mimetics thereof, wherein the two unnatural amino acids replace two of the amino acids at any positions 3 amino acids apart (i and i+3), 4 amino acids apart (i and i+4) or 7 amino acids apart (i and i+7), and wherein the cross-link between the two unnatural amino acids is a C1-C10 alkyl, alkenyl, alkynyl, $(R1\text{-}K\text{-}R1)_n$; each of which is substituted with a 0-6 R2, wherein R1 is an alkyl, alkenyl or alkynyl;

K is O, S, SO, $SO_2$, CO, CONR4, or

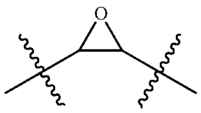
;

R2 is a halo, C1-C10 alkyl, OR3, N(R3)$_2$, SR3, SOR3, SO$_2$R3, CO$_2$R3, R3, a fluorescent moiety or a radioisotope;

R3 is H or a C1-C10 alkyl;

R4 is H, alkyl or a therapeutic agent; and n is an integer from 1-4.

In the above formula, it should be understood that amino acids are only represented by letters within parentheses followed by "wherein the sequence of the amino acids of the peptide comprises". The R's outside of those parentheses (R1, R2, R3, and R4) and the K in "(R1-K-R1)" would be understood to represent variables that are subsequently defined, and the H, C, S outside of those parentheses would be understood to represent the atoms hydrogen, carbon and sulfur, respectively.

It is contemplated that the invention peptides also encompass future variations in known procedures for stabilizing α-helices. For example, it is believed that the methyl group of the unnatural amino acids could be substituted with another small (e.g., C1-C5) alkyl, alkenyl, or alkynyl without affecting the activity of the peptide in vitro or in vivo, or the ability of the cross-link to stabilize the peptide and increase its α-helicity.

As used herein, the designation of an amino acid residue in the instant peptides as more than one amino acid (using the common one-letter amino acid code) in parenthesis with a slash between the amino acids, mean that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

As used herein, a mimetic or peptidomimetic is a compound that is capable of mimicking a natural parent amino acid in a protein, in that the substitution of the peptidomimetic for the natural amino acid does not affect the activity of the protein. Proteins comprising peptidomimetics are generally not substrates of proteases and are likely to be active in vivo for a longer period of time as compared to the natural proteins. In addition, they could be less antigenic and show an overall higher bioavailability. The skilled artisan would understand that design and synthesis of peptidomimetics that could substitute for amino acids of any particular peptide (such as the peptides of this invention) would not require undue experimentation. See, e.g., Ripka et al., 1998; Kieber-Emmons et al., 1997; Sanderson, 1999. Nonlimiting examples of mimetics useful for this invention include D-amino acids and constrained amino acids such as norleucine, or 2-aminoisobutyric acid. It is also within the confines of the present invention that amino acids in the peptide sequence can be substituted with amino acids having a propensity to form alpha helices.

Each peptide of the present invention can include the addition of one or more chemical groups at specific amino acid(s) and/or at the amino end and/or at carboxy end, in order to enhance the stability, reactivity and/or solubility of the peptides. For example, hydrophobic groups such as carbobenzoyl, dansyl, acetyl, a t-butyloxycarbonyl group, or a 9-fluorenylmethyoxycarbonyl group may be added to the amino terminal end of the peptide. In another example, the hydrophobic group, t-butyloxycarbonyl, or an amido group, or a para-nitrobenzyl ester group, may be added to the carboxy terminal end of the peptide. Techniques for introducing such modifications are well known to those of skill in the art.

The peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, succinic or methanesulfonic. Where the peptides of the invention include an acidic moiety, suitable pharmaceutically acceptable salts may include alkali metal salts, such as sodium or potassium salts, or alkaline earth metal salts, such as calcium or magnesium salts. A salt of the peptide in which the amino terminus is H and the carboxy terminus is NH$_2$ is preferred. The present invention also includes the peptides in free acid form.

The amino acid residues for the invention peptides are the combination of the specific peptide identified by Sticht et al. (2005) having the amino acid sequence ITFEDLLDYYGP (SEQ ID NO:1; CAI), along with substitutions in that sequence that were identified by Sticht et al. (2005) in the peptides that most frequently bound to the C-CANC protein used in that work (see Table 1 of Sticht et al., 2005). Also included are amino acids that are conservative substitutions for the Sticht et al. peptide. It is believed that peptides of any combination of the alternative amino acids or mimetics in the sequence provided would inhibit assembly of a capsid-containing virus, in vivo or in vitro (i.e., outside the cell). Such assembly inhibition can be tested without undue experimentation by, e.g., the methods described in the Examples below, or in Sticht et al., 2005.

Preferably, the sequence of the amino acids of the peptide comprises (I/V)(T/S)(F/W/Y)(E/S)(D/E)L(L/D/T)(D/A/S)(Y/F)(Y/M) (SEQ ID NO:3), which is the combination of the specific peptide (SEQ ID NO:1; CAI) identified by Sticht et al., along with substitutions in that sequence that were identified by Sticht et al. in the peptides that most frequently bound to the C-CANC peptide used in that work (Table 1 of Sticht et al., 2005).

It is also preferred that the peptide comprises 11 to 23 amino acids, where the amino acid following (Y/T/I/L/V/M/T) is (G/S/T/N/H/C/L/R/D/E/Q/M/K) (SEQ ID NO:4). The amino acid options for the 11<th> peptide (G/S/T/N/H/C/L/R/D/E/Q/M/K) is identified from Sticht et al., 2005, with conservative substitutions as described above. More preferably, the amino acid following (Y/F/I/L/V/M/T) is G.

It is even more preferred if the peptide comprises 12 to 23 amino acids, wherein the amino acid following (G/S/T/N/H/C/L/R/D/E/Q/M/K) is (P/M/R/K) (SEQ ID NO:5), preferably P. In the most preferred embodiments, the sequence of the amino acids of the peptide comprises ITFEDLLDYYGP (SEQ ID NO: 1).

The preferred cross-link between the two unnatural amino acids is

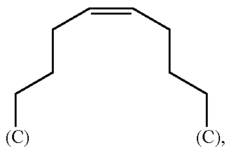

wherein the (C)s are the α-carbons of the unnatural amino acids.

Preferably, the unnatural amino acids are at an i and i+4 positions. Most preferably, they replace the fourth [(D/E/S)] and the eighth [(D/E/S)] amino acids of the peptide, the seventh [(L/D/T/F/I/V/Y/M/W)] and eleventh [(G/S/T/N/H/C/L/R/D/E/Q/M)] amino acids of the peptide, or the eighth [(D/E/S)] and the twelfth [(P/M/R/K)] amino acids of the peptide.

Most preferably, the peptide comprises, or consists of,

SEQ ID NO: 6

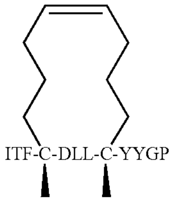

Since the peptides of the present invention can enter cells, they can be used as a delivery system to deliver any additional useful moiety into the cell, for example for proteins, nucleic acids, carbohydrates, metals, etc. Where the peptides comprise an additional moiety to be delivered into the cell, the additional moiety is preferably a detectable moiety, a therapeutic compound, or an antigen. Preferred detectable moieties include fluorescent moieties and radioactive moieties. Where the peptide further comprises an antigen, the antigen can be anything that can elicit a useful immunological response. Non-limiting examples include viral antigens that can induce immunity to a virus and antigens that induce immunity to bacteria, for example *Mycobacterium tuberculosis*, or parasites, e.g., a *Plasmodium falciparum* antigen. A preferred viral antigen is an HIV antigen.

Where the moiety is a therapeutic compound, the compound can be any therapeutic compound now known or later discovered, and includes oligopeptides, for example less than 20 amino acids long, or less than 10 amino acids long. Preferred therapeutic compounds are organic compounds less than 2000 MW, for example an antiviral compound. Such therapeutic compounds can be, for example, in the form of a prodrug that is bound to the rest of the peptide with an ester bond that is susceptible to a cellular esterase, assuring that the therapeutic compound is not released until the peptide enters a cell. Methods of producing such prodrugs are known in the art.

As established in the Examples, the peptide

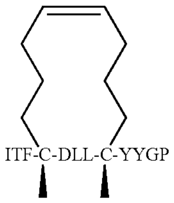

can enter a cell and inhibit HIV reproduction. Without being bound to any particular mechanism, it is believed that the peptide binds to the capsid domain of the HIV gag protein, preventing viral assembly and thus replication. As such, the invention peptides are expected to bind and inhibit replication of any capsid-containing virus. Thus, preferred peptides can inhibit replication of a capsid-containing virus in a cell. Examples of capsid-containing viruses include the Retroviridae, including lentiviruses, such as HIV; Togaviridae including rubella virus; Picornaviridae such as enteroviruses, poliovirus, rhinovirus and hepatitis A virus; Orthomyxoviridae such as influenza virus; Paramyxoviridae such as paramyxoviruses; Herpesviridae such as herpes viruses and cytomegaloviruses; Hepnaviridae such as hepatitis B viruses; Flaviviridae such as flavivirus, hepatitis C virus, tick borne encephalitis, yellow fever and dengue fever viruses; Coronaviridae such as coronaviruses including SARS virus and toroviruses; Filoviridae such as Ebola and Marburg viruses; Bunyaviridae such as hantaviruses and arenaviruses.

The capsid-containing virus is preferably a retrovirus, e.g., HIV, HTLV-I, H and III, a feline immunodeficiency virus, a bovine immunodeficiency virus, a simian immunodeficiency virus, a feline sarcoma or leukemia virus, or a bovine leucosis virus.

More preferably, the peptide inhibits replication of a lentivirus. In the most preferred embodiments, the peptide can inhibit replication of an HIV. It is expected that the peptides could inhibit any strain of HIV, including HIV-1 and HIV-2, since the Examples show that the peptide described above inhibits a wide range of HIV isolates (Table 1).

The invention is also directed to pharmaceutical compositions comprising the above-described peptides that can inhibit assembly of a capsid-containing virus, in a pharmaceutically acceptable carrier.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The invention is additionally directed to methods of inhibiting replication of a capsid-containing virus in a cell. The methods comprise contacting the cell with the above-described peptides that can inhibit a capsid-containing virus, in a manner sufficient to inhibit replication of the capsid-containing virus in the cell.

These methods are useful with any capsid-containing virus. Preferably the virus is a retrovirus, more preferably a lentivirus and most preferably an HIV.

Any prokaryotic, eukaryotic or archaea cell infected with a capsid-containing virus can be treated with the invention peptides. The method can utilize cells in culture (e.g., as in Examples), or preferably in a live multicellular organism, including any plants or animals. More preferably, the cell is part of a live vertebrate infected with the capsid-containing virus. Even more preferably, the cell is in a mammal infected with the capsid-containing virus. Still more preferably, the mammal is a human, most preferably infected with HIV.

Where the virus is in a live mammal, it is contemplated that the present methods could be used in conjunction with at least one other antiviral treatment, for example any antiviral treatment, or combination thereof, used against HIV.

The invention is further directed to methods of treating a mammal infected with a capsid-containing virus. The methods comprise administering the above-described pharmaceutical composition to the mammal in a manner sufficient to treat the mammal. Preferably, the mammal is a human.

These methods are useful with any capsid-containing virus. Preferably the virus is a retrovirus, more preferably a lentivirus and most preferably an HIV.

The peptides for these methods preferably comprises

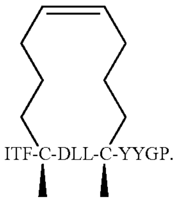

Some applications of these methods comprise treating a pregnant female infected with the virus to reduce the risk of passing the virus to the fetus in utero or to the baby during delivery.

It is contemplated that the present methods could be used in conjunction with at least one other antiviral treatment, for example any antiviral treatment, or combination thereof, used against HIV.

These methods can also be used as a prophylactic against infection with the capsid-containing virus. Thus, the present invention is additionally directed to methods of treating a mammal at risk for infection with a capsid-containing virus. The methods comprise administering the above-described pharmaceutical composition to the mammal in a manner sufficient to treat the mammal.

These methods are useful with any capsid-containing virus. Preferably the virus is a retrovirus, more preferably a lentivirus and most preferably an HIV.

The peptides for these methods preferably comprises

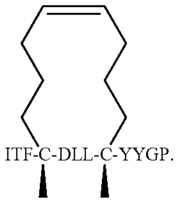

Some applications of these methods comprise treating a fetus in utero having a mother that is infected with the virus to reduce the risk of passing the virus to the fetus in utero or to the baby during delivery.

It is also contemplated that the present methods could be used in conjunction with at least one other antiviral treatment, for example any antiviral treatment, or combination thereof, used against HIV, or any preventative antiviral treatment, including vaccination.

Further, the invention is directed to methods of making any of the above-described peptides. The methods comprise sequentially coupling the amino acids, then joining the two olefinic groups of the unnatural amino acids together using olefin metathesis. These methods are described in, e.g., Schafmeister et al., 2000; Walensky et al., 2004; United States Patent Application Publication 2006/0008848 A1; and PCT Patent Application Publication WO 2005/044839 A2. Preferably, the amino acids are coupled using solid phase synthesis.

The present invention is also directed to the use any of the above-described peptides that can inhibit assembly of a capsid-containing virus for the manufacture of a medicament for the treatment of a mammal infected with a capsid-containing virus.

Additionally, the present invention is directed to the use any of the above-described peptides that can inhibit assembly of a capsid-containing virus for the manufacture of a medicament for the treatment of a mammal to reduce the risk of the mammal becoming infected with a capsid-containing virus.

Also, the invention is directed to the use of the above-described pharmaceutical compositions for the treatment of a mammal infected with a capsid-containing virus.

The invention is additionally directed to the use of the above-described pharmaceutical compositions for the treatment of a mammal at risk for infection with a capsid-containing virus.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Introduction to Examples

The x-ray crystallographic structure of CAI (SEQ ID NO:1) bound to the C-CA was used in the rational modification of CAI using a structure-based approach to form a helical, metabolically stable and cell-penetrating constrained peptide (CPCP). It was reasoned that if the critical amino acids in the CAI that bind to the hydrophobic cleft of the C-CA were preserved and convert the linear peptide to a proteolytically stable cell penetrating peptide, the antiviral potency of the constrained peptide in in vivo could be achieved.

Cell permeability is a prerequisite for any drug to have in vivo activity if the target site is located inside the cell. The lack of cell permeability of peptide-based inhibitors restricts their utility in in vivo applications. Many techniques have been reported which enhance helix structures and metabolic stability of peptides. In some cases, improved binding affinities in in vitro assay have been reported. However, inhibitory potency in vivo or in cell-based assay were seldom reported indicating that these modifications may not render these peptides permeable to cells (Phelan et al., 1997; Leduc et al., 2003; Yang et al., 2004; Wang et al., 2005). Therefore, we resorted to a new and experimentally validated technique of stabilizing α-helicity of linear peptides reported by Schafmeister et al. (Schafmeister et al., 2000). This method was based on an all-hydrocarbon cross-linking system where the amino acids at the i and i+4 or i+7 of the helix were substituted by synthetically constrained amino acids bearing olefinic side chains, which were then cross-linked by olefin metathesis. This technique, termed "hydrocarbon stapling", has been recently successfully applied by Walensky et al. to a BCL-2 homology (BH) protein BH3 in activating apoptosis in vivo (Walensky et al., 2004). The helical and the metabolic stability of the constrained BH3 peptide not only increased substantially it also penetrated cells more efficiently and showed enhanced binding affinity to multidomain BCL-2.

Example 1

Peptide Synthesis

Asymmetric synthesis of (S)-Fmoc-2-(2'-pentenyl)alanine was prepared with Ala-Ni(II)-BPB-complex by the method of Qiu et al. (2000). The constrained peptide having the structure

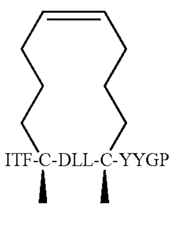

was synthesized manually by Fmoc solid phase synthesis method using Rink amide MBHA resin (0.33 mmol/g). For the normal amino acid, the couplings were performed with fourfold excess of activated amino acids. Fmoc-amino acids were activated using the ratio of Fmoc-amino acid:HBTU:HOBt:DIEA, 1:1:1:2. For (S)-Fmoc-2-(2'-pentenyl)alanine, couplings were performed with twofold excess of amino acid and activated using DIC:HOAt (1:1). For peptide olefin metathesis (Schafmeister, et al., 2000), the peptide resin with N-terminal protected by Fmoc group was treated with degassed 1,2 dichloroethane containing Bis(tricyclohexylphosphine)benzylidine ruthenium (IV) dichloride (10 mM) at room temperature for two hours and the reaction was repeated once for completion. After de-Fmoc, the resin bound peptide was cleaved using standard protocols (95% TFA, 2.5% water, 2.5% TIS). The cleaved peptide was purified by RP-HPLC using 0.1% (v/v) TFA/water and 0.1% (v/v) TFA/acetonitrile and their identities were confirmed using electrospray mass spectroscopy.

For fluorescently labeled peptides, the N-terminal group of the above constrained peptide was further derivatized with 13-Ala and FITC (DMF/DIEA) on the resin before the cleavage. The other cleavage, purification and confirmation steps were same as above.

Example 2

Assessment of Cellular Uptake of the Linear and the Constrained Peptides

Figure 2:
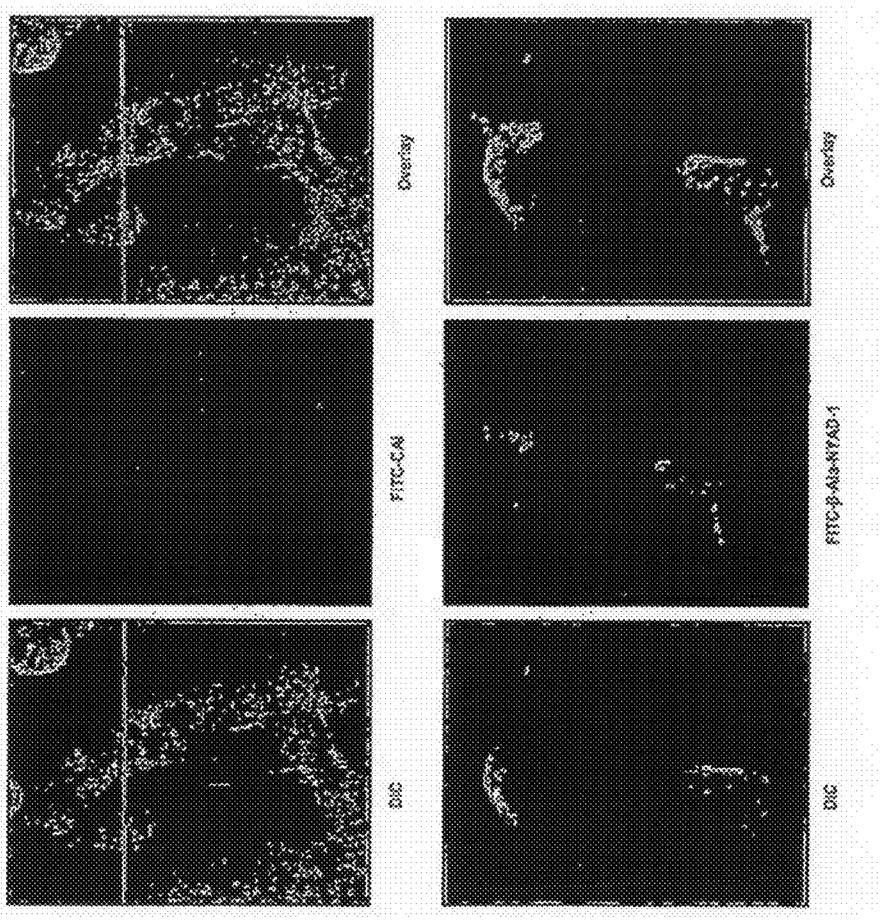
FIG. 2 is micrographs of cells showing that FITC-β-Ala-NYAD-1 penetrates 293T cells. Confocal microscopy images of 293T cells incubated for 20 hours at 37° C. with FITC-conjugated peptide. Cells were washed 3 times with PBS before viewing. Upper panel: Left, Differential Interference Contrast (DIC) image of cells with FITC-CAI. Center, FITC fluorescent image of the same cells with FITC-CAI. Right, Overlay of DIC and FITC fluorescent images. Lower panel: Left, DIC image of cells with FITC-P-Ala-NYAD-1. Center, FITC fluorescent image of the same cells with FITC-β-Ala-NYAD-1. Right, Overlay of DIC and FITC fluorescent images.

In an initial experiment to show that the constrained peptides penetrate the cells, fluorescence-activated cell sorter (FACS) analysis was performed using two different cell types, 293T and MT-2 cells (FIG. 1). However, there are recent reports (Richard et al., 2003; Lundberg et al., 2002) showing that the results in FACS analysis may not conclusively show whether the constrained peptides penetrated cells since peptides may associate with the cell surface. Therefore, a confocal microscopic study was performed to show conclusively that the constrained peptide indeed penetrated the cell membrane and taken up by the cells whereas the linear peptide (CAI) did not penetrate (FIG. 2).

FACS Analysis of FITC-Conjugated Peptide-Treated Cells.

293T and MT2 cells were maintained in RPMI 1640 (Invitrogen), 10% fetal bovine serum, 100 U/ml penicillin, 100 μg/ml streptomycin, 2 mM glutamine, 50 mM HEPES pH 7, and 50 mM β-mercaptoethanol. Cells were seeded into a 24-well plate ($2\times10^4$/well) on the day before treatment with FITC-conjugated peptides. After two washes with 1×PBS, cells were incubated with 5 μM of FITC-conjugated peptide in serum-free medium for 4 hours at 37° C., and then washed three times with 1×PBS and digested with 0.25% trypsin for 30 min at 37° C. After one more wash with 1×PBS, resuspended cells were subjected to FACS analysis (Becton Dickinson). The data indicate that about 40 and 96% of 293T cells were stained positive for FITC-conjugated CAI and for FITC-conjugated NYAD-1, respectively. In contrast, none of the MT-2 cells was stained positive for FITC-conjugated CAI whereas about 92% of MT-2 cells were stained positive for FITC-conjugated NYAD-1.

Confocal Microscopy.

293T and MT2 cells were seeded in the 4-well chamber plates and incubated with FITC-conjugated peptides as described above in serum-free medium for 4 hours or/and additional 16 hours in the complete medium containing serum. After 3 washes with 1×PBS, live cells were examined and imaged under confocal microscope (Zeiss). As shown in FIG. 2, the constrained peptide penetrated the cell membrane and was taken up by the cells, while the linear peptide (CAI) did not penetrate.

Example 3

Inhibition of In Vitro Assembly

Both cell-free and cell-based methods were used to observe the morphological changes of virus like particles after treatment with CAI and NYAD-1.

Cell-Free System.

In vitro assembly systems were set up as described (Huseby, et al, Ganser-Pornillos, et al.) with minor modification. We have used 50 mM $Na_2HPO_4$, pH 8.0 as dialysis buffer. The buffer used for assembly studies also contained 0.1~2 M of NaCl. 500-Da-MWCO dialysis tubes (Spectra/Por) were used for the dialysis of peptides. Briefly, stock proteins were adjusted to the appropriate concentration (25 μM for Gag proteins and 50 μM for CA proteins) with the $Na_2HPO_4$ buffer at pH 8.0. After addition of 5% total *E. coli* RNA (RNA:protein=1:20 by weight), incubation with or without 5-fold excess of CAI or NYAD-1 for 30 min at 4° C., the samples were dialyzed overnight in $Na_2HPO_4$ buffer at pH 8.0 containing 100 mM of NaCl at 4° C. For CA mature-like particles assembly, addition of 5% total *E. coli* RNA was avoided. Negative staining was used to check the assembly. To test the effect of inhibition on the assembled immature or mature virus like particles (VLPs), different concentrations of CAI or NYAD-1 were incubated with VLPs for 30 min at 4° C. Carbon-coated copper grids (200 mesh size; EM Sciences) were treated with 20 μl of poly-L-lysine (1 mg/ml; Sigma) for 2 min. 20 μl of reaction solution was placed onto the grid for 2 min. Spotted grids were then stained with 30 μl of uranyl acetate solution for 2 min. Excess stain was removed, and grids were air-dried. Specimens were examined with a Philips EM410 electron microscope.

Figure 4:
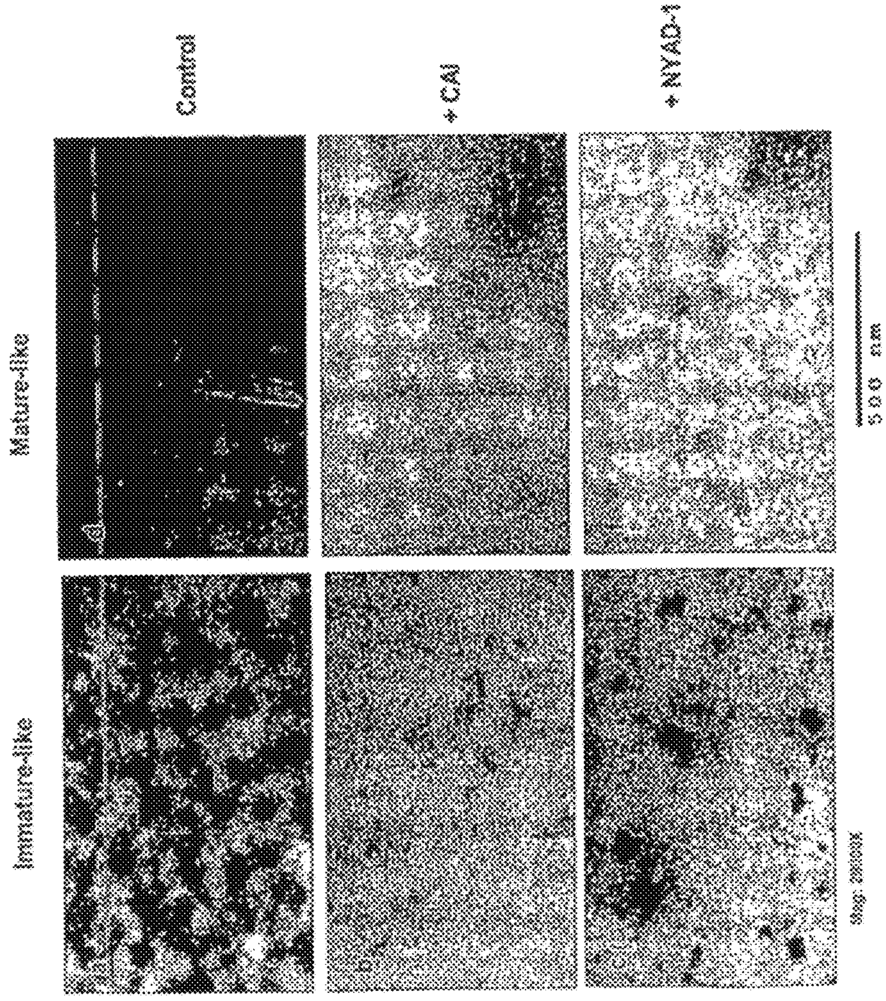
FIG. 4 is electron micrograph images showing the inhibition of assembly of immature-like and mature-like particles in vitro. The images are negatively stained EM images of particles resulting from in vitro assembly of Gag and CA proteins, respectively, in the presence of (a & d) none (control), (b & e) 5× molar excess of CA1, and (c & f) 5× molar excess of NYAD-1.

In order to verify whether NYAD-1 retains the ability to inhibit both immature and mature virus assembly we set up two in vitro assembly systems. We used full-length Gag proteins to form spherical immature-like particles (FIG. 4*a*). After incubation with 5-fold molar excess of CAI or NYAD-1, the particles were completely disrupted (FIG. 4*b* & *c*). For the mature-like particles, we expressed and purified CA protein and obtained tube-shaped particles (FIG. 4*d*). After incubation with 5-fold molar excess of either CAI or NYAD-1, the tube-shaped particles were completely disrupted (FIG. 4*e* & *f*). The rationale for using CA instead of CANC to form the mature-like particles was to confirm that NYAD-1 targets CA only.

Cell-Based System.

To analyze the impacts of NYAD-1 on VLP release, and the morphology of VLPs, electron microscopy was conducted 1 day post-transfection with plasmid encoding Gag or Gag-pol. $4\times10^5$ 293 T cells were seeded per well in a 6-well-plate on the day before transfection. Cells were washed twice after 4 hours' transfection and incubated with complete culture medium in the presence or absence of NYAD-1 at different concentrations for another 20 hours. Cells were fixed in 3% gluteraldehyde in 100 mM sodium cacodylate for 1 hour and post-fixed in 1% $OsO_4$ in 100 mM sodium cacodylate for another 1 hour. Specimens were then dehydrated through graded series of ethanol solutions and embedded in EPON media. After staining with uranyl acetate and lead citrate, ultra-thin sections were examined under a Philips EM410 electron microscope at 80 Kv.

Figure 5:
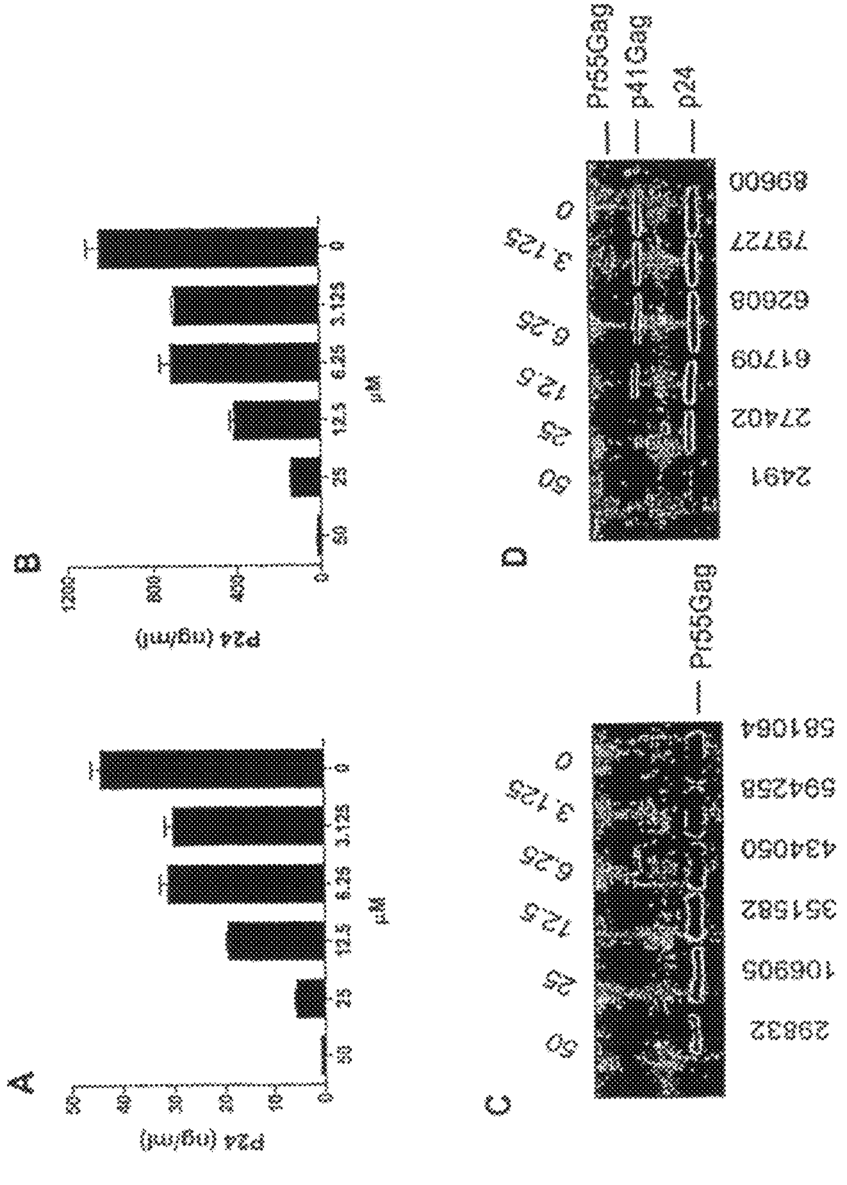
FIG. 5 shows the effect of NYAD-1 on virus-like particle (VLP) release. 293T cells were treated with different concentrations of NYAD-1 4 hours post-transfection with vector encoding Gag (for immature-like particles) or Gag-pol (for mature-like particles). The VLP-containing supernatant was recovered 48 hours post-transfection. The immature- and mature-like particle release was determined by measuring p24 by ELISA (upper panel A, B) and Western blot (lower panel C, D). Numbers below the blots indicate the signal intensities obtained by densitometry.

To confirm that NYAD-1 disrupts immature- and mature-like particles in cells we employed ELISA, Western blot and electron microscopy (EM) to evaluate released particles both quantitatively and qualitatively. The ELISA results indicated a dose-dependent inhibition of the release of virus-like particles when Gag-transfected 293T cells were treated with NYAD-1 at graded concentrations. At 50 μM dose about 72-fold reduction of the release of immature-like particles was observed compared to the untreated cells (FIG. 5A). A similar result (67-fold reduction) is obtained with Gag-pol transfected 293T cells treated with NYAD-1 (FIG. 5B). The Western blot experiments performed with the supernatant also confirmed similar trends in inhibition of both Gag- (FIG. 5C) and Gag-pol-transfected cells treated with NYAD-1 (FIG. 5D).

Figure 6:
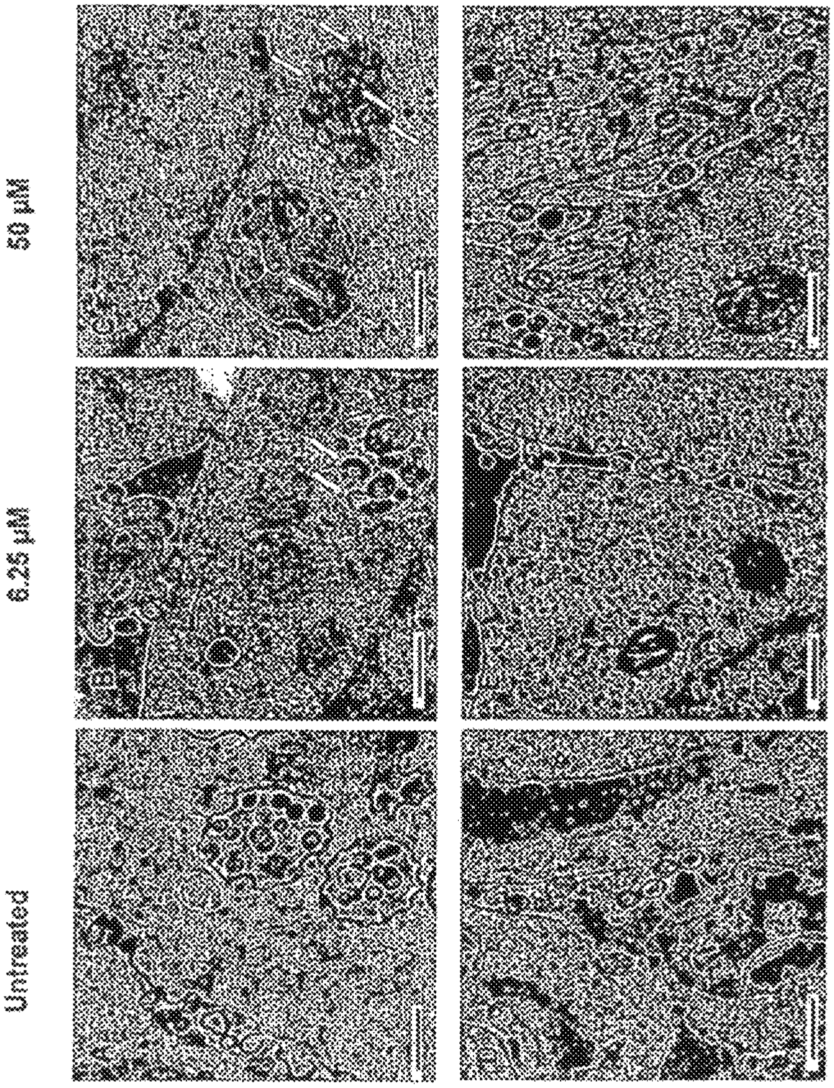
FIG. 6 is an electron microscopic analysis of HIV-1 virus-like particles produced in the presence of 6.25 μM and 50 μM NYAD-1. 293T cells expressing Gag (upper panel) or Gag-pol (lower panel) were incubated with 2 ml culture medium containing none or 6.25 μM and 50 μM of NYAD-1 4 hours post-transfection with vector encoding Gag or Gag-pol. 24 hours post-transfection, cells were pelleted, fixed, embedded, sectioned, and examined with a transmission electron microscope. (Bar=500 nm.)

Electron microscopic analysis of the untreated Gag-transfected 293T cells showed distinct immature-like particles (FIG. 6A). However, when the cells were treated with 6.25 or 50 μM NYAD-1, a majority of the particles have an aberrant shape (FIGS. 6B and C). In case of untreated Gag-pol transfected 293T cells, a large number of mature-like particles containing electrodense core structures were found (FIG. 6D). When these cells were treated with 6.25 or 50 μM NYAD-1 the electrodense core structures were lost in the released virus-like particles (VLPs) (FIGS. 6E & F). Taken together, these data confirm that NYAD-1 targets Gag and impairs the organization of Gag or its products at the cellular level.

Example 4

Inhibition of Viral Replication and Assessment of In Vitro Cytotoxicity

MT-2 and PBMC cells and several laboratory-adapted strain of HIV-1, such as, HIV-1 IIIB, BaL, SF2, SF162, 93N101, 93US657, 93MW959, 92RW008, etc, including AZT-resistant isolates, were used for the virus inhibition assays. Cell lines and the HIV-1 strains can be obtained through the NIH AIDS Research and Reference Reagent Program.

The inhibitory activity of the constrained peptide described in Example 1 on infection by laboratory-adapted HIV-1 strains was determined as described in Jiang et al. (1991). In brief, $1\times10^4$ MT-2 cells were infected with HIV-1 at 100 $TCID_{50}$ (50% tissue culture infective dose) (0.01MOI) in 200 μl RPMI 1640 medium containing 10% FBS in the presence or absence of peptides at graded concentrations overnight. The culture supernatant was then removed and fresh media was added. On the fourth day post-infection, 100 μl of culture supernatants was collected from each well, mixed with equal volumes of 5% Triton X-100 and assayed for p24 antigen by ELISA using a kit from Coulter Immunology (Hialeah, Fla.) and presented in Table 1.

Inhibitory activity of the peptides on infection by primary HIV-1 isolates was determined by the method described in Jiang et al. (2004). PBMCs were isolated from the blood of healthy donors at the New York Blood Center by standard density gradient centrifugation using Histopaque-1077 (Sigma). The cells were cultured at 37° C. for 2 h. The non-adherent cells were collected and resuspended at $5\times10^6$ cells/ml RPMI-1640 medium containing 10% FBS, 5 μg/ml PHA and 100 U/ml IL-2 (Sigma-Aldrich), followed by incubation at 37° C. for 3 days. The PHA-stimulated cells ($5\times10^4$) were infected with corresponding primary HIV-1 isolates at 500 $TCID_{50}$ in the absence or presence of peptides at graded concentrations. Culture media were changed every 3 days. The supernatants were collected 7 days post-infection and tested for p24 antigen by ELISA. The percent inhibition of p24 production was calculated and $IC_{50}$ values were calculated using the GraphPad Prism software (GraphPad Software Inc., San Diego, Calif.) and presented in Table 1.

The in vitro cytotoxicity of the constrained peptide in MT-2 cells and PBMCs was measured by a colorimetric method using XTT (sodium 3'-(1-(phenylamino)-carbonyl)-3,4-tetrazolium-bis(4-methoxy-6-nitro) benzenesulfonic acid hydrate), a light yellowish tetrazolium dye, as reported in a prior art (Jiang et al., 2004). Briefly, for MT-2 cells, 100 μl of a peptide at graded concentrations was added to equal volume of cells ($5\times10^5$/ml) in wells of 96-well plates followed by incubation at 37° C. for 4 days, which was run in parallel to the neutralization assay in MT-2 with only difference of adding medium instead of virus. In the case of PBMC, $5\times10^5$ cells/ml were used and the cytotoxicity was measured after 7 days. After addition of XTT (PolySciences, Inc., Warrington, Pa.), the soluble intracellular formazan was quantitated colorimetrically at 450 nm 4 h later with a reference at 620 nm. The percent of cytotoxicity and the $CC_{50}$ (the concentration for 50% cytotoxicity) values were calculated using the GraphPad Prism software (GraphPad Software Inc., San Diego, Calif.) and listed in Table 1.

NYAD-1 showed inhibition of both immature- and mature-like particles in cell-free as well as cell-based assembly systems. However, our goal was to confirm its anti-HIV-1 activity in a cell-based assay using several laboratory-adapted and primary isolates in MT-2 cells and PBMC, respectively. The inhibition of p24 production in MT-2 cells by NYAD-1 was measured over a range of concentrations and the concentration required to inhibit 50% of the p24 production ($IC_{50}$) was calculated. The results in Table 1 indicate that NYAD-1 efficiently inhibited a broad range of HIV-1 strains, representing different subtypes, which use R5, X4 or R5X4 coreceptors. NYAD-1 inhibited the laboratory strains with low μM potency ($IC_{50}$~4-15 μM), and both R5- and X4-tropic viruses were inhibited with similar potency. We also tested one X4-tropic RT-resistant (AZT) strain in MT-2 and one dual tropic (R5X4) RT-resistant (AZT) strain in PBMC and NYAD-1 inhibited the dual-tropic resistant virus with slightly higher potency.

We tested the inhibition of NYAD-1 against a panel of HIV-1 primary isolates in PBMC representing mostly group M (subtypes from A to G) with diverse coreceptor usage. NYAD-1 showed inhibition against all primary isolates tested including one from group O (Table 1). However, the $IC_{50}$ values against this virus (BCF02) as well as one from Glade E (93TH051) were slightly higher. The inhibitory activities against this diverse range of primary isolates were similar indicating its effectiveness against a wide range of HIV-1 isolates.

The cytotoxicity of NYAD-1 was assessed by the XTT method in both MT-2 cells and PBMC. Cytotoxicity assays were performed in parallel to the HIV-1 inhibition assays. The $CC_{50}$ (concentration of inhibitor required to produce 50% cytotoxicity) values for MT-2 and PBMC were >135 and >300 μM, respectively.

Table 1. Antiviral activity of the constrained peptide NYAD-1, in laboratory-adapted and primary HIV-1 isolates

TABLE 1

Antiviral activity of the constrained peptide NYAD-1, in laboratory-adapted and primary HIV-1 isolates

| HIV-1 Virus | Primary Clade | Cell Type | Coreceptor use | IC50 (μM) ± SD* |
|---|---|---|---|---|
| Laboratory-Adapted | | | | |
| IIIB | B | MT-2 | X4 | 6.22 ± 0.75 |
| MN | B | MT-2 | X4 | 6.79 ± 0.65 |
| RF | B | MT-2 | X4 | 4.29 ± 0.42 |
| V32 | B | MT-2 | X4 | 7.91 ± 0.70 |
| BaL | B | PBMC | X4 | 6.47 ± 0.85 |
| SF162 | B | PBMC | R5 | 15.44 ± 3.23 |
| AZT-Resistant | | | | |
| AZT-R | B | MT-2 | X4 | 16.28 ± 2.79 |
| A17 | B | PBMC | R5X4 | 10.55 ± 1.56 |

TABLE 1-continued

Antiviral activity of the constrained peptide NYAD-1, in laboratory-adapted and primary HIV-1 isolates

| HIV-1 Virus | Primary Clade | Cell Type | Coreceptor use | IC50 (μM) ± SD* |
|---|---|---|---|---|
| Primary Isolates | | | | |
| 92RW008 | A | PBMC | R5 | 12.12 ± 1.64 |
| 92UG029 | A | PBMC | X4 | 13.85 ± 1.34 |
| 92US657 | B | PBMC | R5 | 10.54 ± 2.78 |
| 93IN101 | C | PBMC | R5 | 16.48 ± 0.47 |
| 93MW959 | C | PBMC | R5 | 16.49 ± 2.83 |
| 92UG001 | D | PBMC | R5X4 | 9.14 ± 0.27 |
| CMU02 | E | PBMC | X4 | 10.03 ± 0.81 |
| 93TH051 | E | PBMC | R5X4 | 20.50 ± 1.90 |
| 93BR020 | F | PBMC | R5X4 | 6.60 ± 1.60 |
| RU570 | G | PBMC | R5 | 9.79 ± 2.49 |
| BCF02 | (Group O) | PBMC | R5 | 21.60 ± 3.04 |

*The linear peptide CAI did not show any activity up to 200 μM dose level. The $CC_{50}$ value in MT-2 cells was >135 μM; and in PBMC cells was >300 μM.

Example 5

Hydrocarbon Stapling Enhanced α-Helicity of NYAD-1

We used Circular Dichroism (CD) to characterize the secondary structure of NYAD-1 and CM in the uncomplexed state in solution. CD spectra were obtained on a Jasco J-715 Spectropolarimeter (Jasco Inc, Japan) at 20° C. using the standard measurement parameters in Tris-HCl buffer (20 mM Tris, pH8.0) in the presence of 1-15% (vol/vol) acetonitrile at a final concentration of 125-500 μM. In all the samples, the final concentrations of peptides and salt were always the same, and the spectra were corrected by subtracting the CD spectra of the appropriate reference solvent. % α-helix was calculated from molar ellipticity [Θ] value at 222 nm. The CD spectrum of CAI did not show typical helix minima at 222 and 208 nm, rather a strong minimum at 205 nm was observed indicative of random coil structure in solution. This supports a binding induced conformational change of the CM peptide in complex with C-CA. In contrast, the CD spectrum of NYAD-1 showed distinct minima at both 222 and 208 nm. The α-helicity of NYAD-1, calculated from the molar elipticity value at 222 nm, is ~80%. The results confirm our hypothesis that hydrocarbon stapling enhances the α-helicity of CAI.

Example 6

NYAD-1 Colocalizes with HIV-1 Gag

Figure 3:
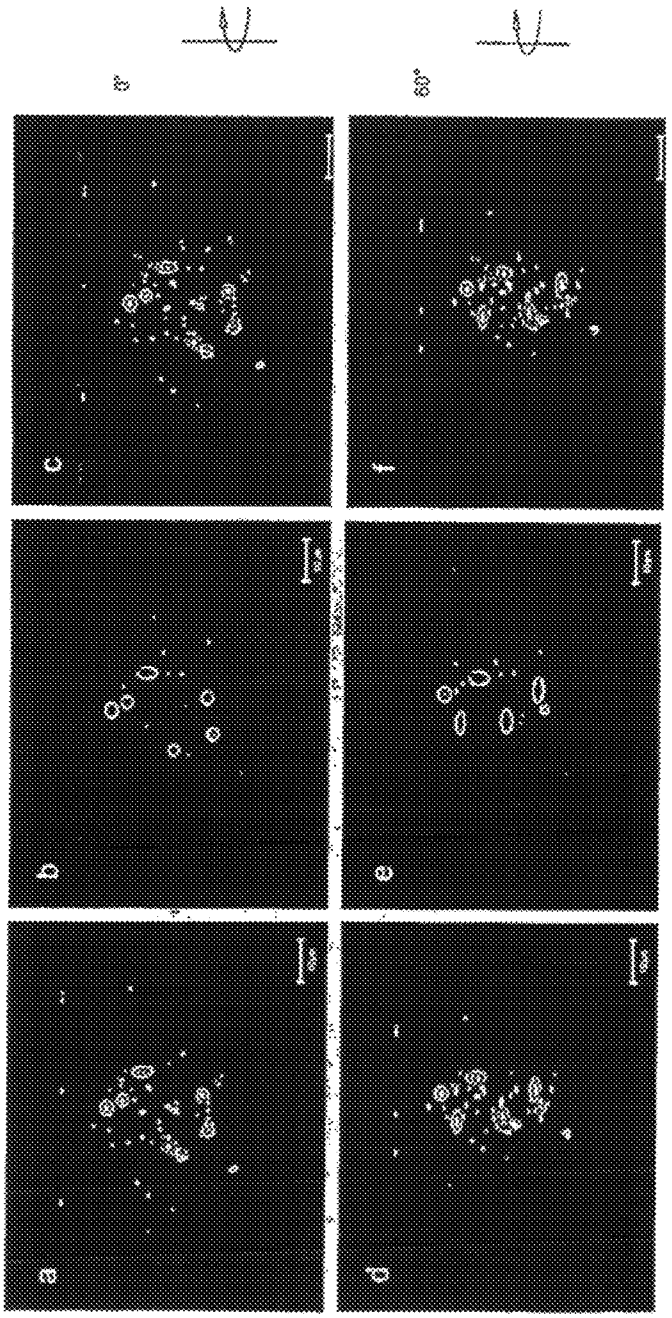
FIG. 3 shows a direct colocalization study of NYAD-1 and Gag by Confocal microscopy. Images at different angles were shown. (a & d) FITC-conjugated NYAD-1. (b & e) Gag-mStrawberry. (c, f) Merged views demonstrated colocalization of FITC-NYAD-1 with Gag-mStrawberry. All samples were living cells and obtained 24 hours post-transfection.

Although NYAD-1 penetrates cells it does not guarantee that it will colocalize and interact with the Gag polyprotein to inhibit viral assembly. To address this concern, we performed a direct colocalization experiment using HIV-1 Gag-mStrawberry fusion protein and FITC-conjugated NYAD-1. A direct colocalization study was performed by transfecting 293T cells with pEF6A-Gag-mStrawberry for 4 hours and then washing cells once with PBS. A serum-free or serum-containing medium containing FITC-conjugated peptide was added for another 20 hours culture. After three washes, the cells were examined and imaged under a Zeiss LSM510 laser scanning confocal microscope (Zeiss). When Gag-mStrawberry transfected cells were exposed to the FITC-conjugated NYAD-1, significant fraction colocalized [FIG. 3, data shown at two different angles] near the plasma membrane. The colocalization data firmly establish the cell permeability of NYAD-1 and suggest interactions with the Gag polyprotein.

Example 7

NMR Mapping of the Binding Site of NYAD-1

Chemical shift difference mapping was used to characterize the C-CA binding site interactions of NYAD-1. Owing to the poor solubility of NYAD-1 in aqueous buffer (~10 μM) a second peptide identical in sequence with three lysines at the C-terminal end (NYAD-13; SEQ ID NO:7) was synthesized using the same protocol. NYAD-13 was highly soluble (~10 mM) in aqueous buffer and used for the NMR studies.

NMR Samples.

Uniformly $^{15}N$- and $^{15}N/^{13}C$-enriched protein samples of C-CA (W184A/M185A) were produced by expressing the pET14b plasmid encoding the mutant C-CA gene in *E. coli* BL21 (DE3) cells cultured in M9-minimal medium containing $^{15}NH^4Cl$ (Cambridge Isotope Laboratories) and $[^{13}C_6]$-Glucose as sole nitrogen and carbon source respectively. Recombinant proteins were isolated from bacteria and the integrity of the samples confirmed by mass spectrometry. The NMR samples were prepared in a buffer containing 100 mM ammonium acetate pH 7.0, 95% $H_2O$/5% $D_2O$ and 2-10 mM DTT. The protein concentrations were determined from the UV absorbance at 280 nm using an extinction coefficient of 2980 $M^{-1}$ $cm^{-1}$.

NMR Resonance Assignments.

Backbone assignments of C-CA in the absence of peptide were made on a 380 μM [U-$^{15}N$, $^{13}C$] sample. Triple resonance experiments HNCA, HN(CO)CA, HNCACB, CBCA (CO)NH, HNCO and HN(CA)CO were acquired at 298° K on a Bruker AVANCE 700 MHz spectrometer equipped with a Z-axis gradient TXI CryoProbe.

Owing to the poor solubility of NYAD-1, triple resonance experiments of the complex with C-CA were not feasible. However, the $^1H$-$^{15}N$-HSQC spectra of C-CA bound to NYAD-1 and NYAD-13 are nearly identical and we decided to pursue the assignments of the latter bound to C-CA and transfer the assignments to the complex with NYAD-1. A sample of [U-$^{15}N$, $^{13}C$] C-CA in the presence of unlabeled NYAD-13 peptide was prepared at 1:1 molar ratio under identical buffer conditions. The final protein concentration of this sample was ~1.9 mM. The backbone experiments used for assignment were acquired at 298° K on a Bruker AVANCE 500 MHz spectrometer equipped with a Z-axis gradient TXI CryoProbe.

All data were processed in Topspin 1.3 and analyzed using CARA1.5. The backbone chemical shifts of 79 out of 84 (5 Pro) residues were assigned in the free and NYAD-13 complexed states of C-CA.

NMR Perturbation Assay.

The NMR based titrations were carried out with both NYAD-1 and NYAD-13. The NMR based titrations were carried out at 298° K on a Bruker AVANCE 900 MHz spectrometer equipped with a z-axis gradient TCI CryoProbe. Small aliquots of 5-10 μl 3.77 mM unlabeled NYAD-13 in identical buffer conditions were added to 500 μl of 256 μM [U-$^{15}N$] C-CA sample in $NH_4Ac$ buffer, 5% $D_2O$, pH 7.0 and 10 mM DTT. The final peptide:protein ratio was 1:1.8. A 2D $^1H^{15}N$-HSQC spectrum was acquired after each addition. The data were processed in Topspin 1.3 and analyzed in NMR ViewJ v6.12.

A second perturbation assay was carried out by adding 6 μl of 100 mM NYAD-1 in 100% DMSO to 500 μl of 76 μM [U-$^{15}N$] C-CA sample in $NH_4Ac$ buffer, 95% $H_2O$/5% $D_2O$, pH 7.0 and 10 mM DTT.

Calculation of Binding Constant of NYAD-13 from NMR Data.

Owing to the poor solubility of NYAD-1, the binding constant could be calculated only for NYAD-13 from the NMR titration data. The binding of the peptide to C-CA was slow on the NMR timescale and at each peptide to protein ratio two sets of peak were observed, for the bound and free protein respectively. The fraction of bound protein was calculated from the change in relative intensities of the two peaks through the titration and fitted to a standard equation to get a $K_d$ of 1.2±0.6 μM. A second method used the linewidth at half height of the bound protein to calculate the $k_{off}$ rate. A $K_d$ of 0.2±0.1 μM was calculated from the ratio of the experimentally determined $k_{off}$ and a diffusion limited $k_{on}$~$10^8$ $M^{-1}$ $s^{-1}$.

The measurement of chemical shifts during the titration of NYAD-1 with C-CA revealed large changes in the amide hydrogen and nitrogen chemical shifts that have been mapped onto the structure of C-CA. Assignments in free protein and complexes were obtained as described in Methods. The most significant changes map to residues 169 to 190, which include Helix-1 (161-174) and Helix-2 (180-192). These results are in complete agreement with the X-ray structure of CAI bound to wild-type protein and the NMR mapping studies of CAI bound to C-CA (W184A/M185A). The strong similarities in the chemical shift difference profiles of NYAD-1 and CAI bound to C-CA argue in favor of very similar binding modes.

CAI had been shown to form an amphipathic helix which makes important hydrophobic (Helix-1) and N-terminal capping interactions (Helix-2) within the binding pocket of C-CA. The C-terminal end of the CAI peptide is completely exposed to the solvent. Presumably, NYAD-1 binds in a similar fashion since our design strategy did not alter those residues of CAI crucial for binding C-CA. The role of the bulky olefinic link was of some concern but appeared not to perturb the interactions at the binding site. As was the goal of the original design, the linker is on the solvent exposed surface of the bound peptide.

The low solubility of NYAD-1 interfered with a reliable estimate of $K_d$ by NMR. However, the slow exchange kinetics of binding monitored by NMR supports an upper bound on the $K_d$ of c. 10 μM. The binding of a highly soluble NYAD-1 analog, NYAD-13, is identical to NYAD-1 in all respects and yields a $K_d$ of ~1 μM by NMR.

Based on the NMR chemical shift mapping studies we conclude that hydrocarbon stapling of CAI does not alter the principal interactions in the binding site of C-CA and the affinity is in the low micromolar range.

REFERENCES

Abdurahman, S., Hoglund, S., Goobar-Larsson, L., & Vahlne, A. Selected amino acid substitutions in the C-terminal region of human immunodeficiency virus type 1 capsid protein affect virus assembly and release. J Gen Virol 85, 2903-2913 (2004).

Chien, A. I., Liao, W. H., Yang, D. M., & Wang, C. T. A domain directly C-terminal to the major homology region of human immunodeficiency type 1 capsid protein plays a crucial role in directing both virus assembly and incorporation of Gag-Pol. Virology. 348, 84-95 (2006).

Chu, H. H., Chang, Y. F., & Wang, C. T. Mutations in the alpha-helix Directly C-terminal to the Major Homology Region of Human Immunodeficiency Virus Type 1 Capsid Protein Disrupt Gag Multimerization and Markedly Impair Virus Particle Production. J. Biomed. Sci. 13, 645-56 (2006).

Derdeyn, C. A. et al. J. Virol. 74, 8358 (2000).

Derdowski, A., Ding, L., & Spearman, P. A Novel Fluorescence Resonance Energy Transfer Assay Demonstrates that the Human Immunodeficiency Virus Type 1 Pr55Gag I Domain Mediates Gag-Gag Interactions. The Journal of Virology 78, 1230-1242 (2004).

Dong, X. et al. AP-3 directs the intracellular trafficking of HIV-1 Gag and plays a key role in particle assembly. Cell. 120, 663-674 (2005).

Douglas, C. C., Thomas, D., Lanman, J., & Prevelige, P. E., Jr. Investigation of N-terminal domain charged residues on the assembly and stability of HIV-1 CA. Biochemistry. 43, 10435-10441 (2004).

Forshey, B. M., von Schwedler, U., Sundquist, W. I., & Aiken, C. Formation of a human immunodeficiency virus type 1 core of optimal stability is crucial for viral replication. J. Virol. 76, 5667-5677 (2002).

Freed, E. O. HIV-1 gag proteins: diverse functions in the virus life cycle. Virology. 251, 1-15 (1998).

Garzon, M. T. et al. The dimerization domain of the HIV-1 capsid protein binds a capsid protein-derived peptide: a biophysical characterization. Protein Sci 13, 1512-1523 (2004).

Ganser-Pornillos, B. K., von Schwedler, U. K., Stray, K. M., Aiken, C., & Sundquist, W. I. Assembly properties of the human immunodeficiency virus type 1 CA protein. J Virol 78, 2545-2552 (2004).

Gottlinger, H. G. The HIV-1 assembly machine. AIDS Suppl 5, S13-S20 (2001).

Grigorov, B., Arcanger, F., Roingeard, P., Darlix, J. L., & Muriaux, D. Assembly of infectious HIV-1 in human epithelial and T-lymphoblastic cell lines. J Mol. Biol. 359, 848-862 (2006).

Gross, I. et al. J. Virol 72, 4798 (1998).

Guo, X. et al. The R362A mutation at the C-terminus of CA inhibits packaging of human immunodeficiency virus type 1 RNA. Virology 343, 190-200 (2005).

Hoglund, S. et al. Tripeptide interference with human immunodeficiency virus type 1 morphogenesis. Antimicrob. Agents Chemother. 46, 3597-3605 (2002).

Huseby, D., Barklis, R. L., Alfadhli, A., & Barklis, E. Assembly of human immunodeficiency virus precursor gag proteins. J. Biol. Chem. 280, 17664-17670 (2005).

Jiang, S., et al. Journal of Experimental Medicine 174, 1557-1563 (1991).

Jiang, S. et al. Antimicrobial Agents and Chemotherapy 48, 4349-4359 (2004).

Joshi, A., Nagashima, K., & Freed, E. O. Mutation of dileucine-like motifs in the human immunodeficiency virus type 1 capsid disrupts virus assembly, gag-gag interactions, gag-membrane binding, and virion maturation. J. Virol. 80, 7939-7951 (2006).

Kieber-Emmons et al. Curr. Opin. Biotechnol. 8, 435-441 (1997).

Kramer, B. et al. HIV interaction with endosomes in macrophages and dendritic cells. Blood Cells Mol. Dis. 35, 136-142 (2005).

Leduc, A. M. et al. Helix-stabilized cyclic peptides as selective inhibitors of steroid receptor-coactivator interactions. Proc Natl Acad Sci USA. 100, 11273-11278 (2003).

Li, F. et al. PA-457: a potent HIV inhibitor that disrupts core condensation by targeting a late step in Gag processing. Proc Natl Acad Sci USA 100, 13555-13560 (2003).

Morikawa, Y. HIV capsid assembly. Curr HIV Res 1, 1-14 (2003).

Lundberg, M. et al. Biochem. Biophys. Res. Commun., 291, 367 (2002).

Niedrig, M. et al. Inhibition of infectious human immunodeficiency virus type 1 particle formation by Gag protein-derived peptides. J Gen Virol 75 (Pt 6), 1469-1474 (1994).

Nydegger, S., Foti, M., Derdowski, A., Spearman, P., & Thali, M. HIV-1 egress is gated through late endosomal membranes. Traffic. 4, 902-910 (2003).

Ono, A. & Freed, E. O. Cell-type-dependent targeting of human immunodeficiency virus type 1 assembly to the plasma membrane and the multivesicular body. J. Virol. 78, 1552-1563 (2004).

Pelchen-Matthews, A., Kramer, B., & Marsh, M. Infectious HIV-1 assembles in late endosomes in primary macrophages. J. Cell Biol. 162, 443-455 (2003).

Phelan, J. C., Skelton, N. J., Braisted, A. C., & McDowell, R. S. A General Method for Constraining Short Peptides to an a-Helical Conformation. J. Am. Chem. Soc. 119, 455-460 (1997).

Qiu, W. et al. Tetrahedron, 56, 2577 (2000).

Richard, J P et al. J. Biol. Chem., 278, 585 (2003).

Ripka et al. Curr. Opin. Chem. Biol. 2, 441-452 (1998).

Sakalian, M. et al. 3-O-(3',3'-dimethysuccinyl) betulinic acid inhibits maturation of the human immunodeficiency virus type 1 Gag precursor assembled in vitro. J Virol 80, 5716-5722 (2006).

Sanderson. Med. Res. Rev. 19, 179-197 (1999).

Schafmeister, C. E., Po, J., & Verdine, G. L. An All-Hydrocarbon Cross-Linking System for Enhancing the Helicity and Metabolic Stability of Peptides. J. Am. Chem. Soc. 122, 5891-5892 (2000).

Sherer, N. M. et al. Visualization of retroviral replication in living cells reveals budding into multivesicular bodies. Traffic. 4, 785-801 (2003).

Sticht, J. et al. A peptide inhibitor of HIV-1 assembly in vitro. Nat. Struct. Mol. Biol. 12, 671-677 (2005).

Tang, C. et al. Antiviral inhibition of the HIV-1 capsid protein. J Mol. Biol. 327, 1013-1020 (2003).

Ternois, F., Sticht, J., Duquerroy, S., Krausslich, H. G., & Rey, F. A. The HIV-1 capsid protein C-terminal domain in complex with a virus assembly inhibitor. Nat. Struct. Mol. Biol. 12, 678-682 (2005).

Wang, D., Liao, W., & Arora, P. S. Enhanced Metabolic Stability and Protein-Binding Properties of Artificial Helices Derived from a Hydrogen-Bond Surrogate: Application to Bcl-xL. Angewandte Chemie International Edition 44, 6525-6529 (2005).

Walensky, L. D. et al. Activation of Apoptosis in Vivo by a Hydrocarbon-Stapled BH3 Helix. Science 305, 1466-1470 (2004).

Yang, B., Liu, D., & Huang, Z. Synthesis and helical structure of lactam bridged BH3 peptides derived from pro-apoptotic Bcl-2 family proteins. Bioorganic & Medicinal Chemistry Letters 14, 1403-1406 (2004).

United States Patent Application Publication 2006/0008848 A1.

PCT Patent Application Publication WO 2005/044839 A2.

APPENDIX—SEQ ID NO:

SEQ ID NO:1—Antiviral Peptide

ITFEDLLDYYGP

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An isolated peptide from 10 to 23 amino acids long, wherein the sequence of the amino acids of the isolated peptide comprises (I/L/V)(T/S/A/V/C)(F/I/L/V/Y/M/W)(D/E/S)(D/E)(L/F/I/V/Y/M/W)(L/D/T/F/I/V/Y/M/W)(D/E/A/S)(Y/F/I/L/V/M/W)(Y/F/I/L/V/M/T) (SEQ ID NO:2), wherein two of the amino acids are unnatural amino acids having either R or S stereochemistry at the α-carbon, wherein the unnatural amino acids are each (S)-α-2-(4'-pentenyl)alanine or (S)-α-2-(7'-octenyl)alanine, wherein the α-carbon of the unnatural amino acids comprises a methyl group and an olefinic group, where the two olefinic groups of the unnatural amino acids are on the same side of the α-helix and are joined to form a cross-link between the two unnatural amino acids, wherein the two unnatural amino acids replace two of the amino acids at any positions selected from the group consisting of 4 amino acids apart (i and i+4) and 7 amino acids apart (i and i+7); and wherein the cross-link between the two unnatural amino acids is a C1-C10 alkyl, alkenyl, alkynyl, or (R1-K-R1)$_n$; each of which is substituted with a 0-6 R2, wherein R1 is an alkyl, alkenyl, or alkynyl;

K is O, S, SO, $SO_2$, CO, CONR4, or

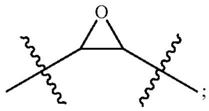 [SMILES: *C1OC1*]

;

R2 is a halo, C1-C10 alkyl, OR3, $N(R3)_2$, SR3SOR3, $SO_2R3$, $CO_2R3$, R3, a fluorescent moiety, or a radioisotope;

R3 is H or a C1-C10 alkyl;

R4 is H, alkyl, or a therapeutic agent; and n is an integer from 1-4.

2. The peptide of claim 1, wherein the sequence of the peptide comprises (I/V)(T/S)(F/W/Y)(E/S)(D/E)L(L/D/T)(D/A/S)(Y/F)(Y/M) (SEQ ID NO:3).

3. The peptide of claim 1, comprising 11 to 23 amino acids, wherein the amino acid following (Y/F/I/L/V/M/T) is (G/S/T/N/H/C/L/R/D/E/Q/M/K) (SEQ ID NO:4).

4. The peptide of claim 3, wherein the sequence of the peptide comprises SEQ ID NO:8.

5. The peptide of claim 3, comprising 12 to 23 amino acids, wherein the amino acid following (G/S/T/N/H/C/L/R/D/E/Q/M/K) is (P/M/R/K) (SEQ ID NO:5).

6. The peptide of claim 5, wherein the sequence of the peptide comprises SEQ ID NO:9.

7. The peptide of claim 6, wherein the sequence of the peptide comprises ITFXDLLXYYGP (SEQ ID NO:6) and wherein X represents the unnatural amino acids.

8. The peptide of claim 1, wherein the cross-link between the two unnatural amino acids is

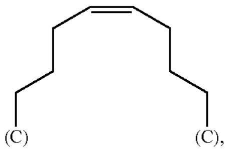

, wherein the (C)s are the α-carbons of the unnatural amino acids.

9. The peptide of claim 1, wherein the peptide comprises SEQ ID NO:10.

10. The peptide of claim 3, wherein the peptide comprises SEQ ID NO:11.

11. The peptide of claim 5, wherein the peptide comprises SEQ ID NO:12.

12. The peptide of claim 1, comprising (SEQ ID NO: 6)

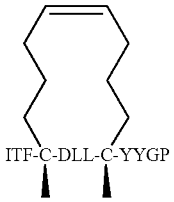

wherein the (C)s are the α-carbons of the unnatural amino acids.

13. The peptide of claim 1, consisting of (SEQ ID NO: 6)

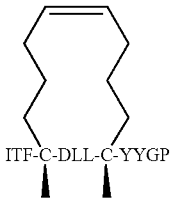

wherein the (C)s are the α-carbons of the unnatural amino acids.

14. The peptide of claim 1, further comprising a detectable moiety, a therapeutic compound, or an antigen.

15. The peptide of claim 14, wherein the detectable moiety is a fluorescent moiety.

16. The peptide of claim 14, wherein the detectable moiety is a radioactive moiety.

17. The peptide of claim 14, further comprising an antigen.

18. The peptide of claim 17, wherein the antigen is a human immunodeficiency virus antigen.

19. The peptide of claim 14, further comprising a therapeutic compound.

20. The peptide of claim 19, wherein the therapeutic compound comprises an oligopeptide less than 20 amino acids long.

21. The peptide of claim 19, wherein the therapeutic compound comprises an oligopeptide less than 10 amino acids long.

22. The peptide of claim 19, wherein the therapeutic compound is an organic compound.

23. The peptide of claim 22, wherein the organic compound is an antiviral compound.

24. The peptide of claim 19, wherein the therapeutic compound is bound to the rest of the peptide with an ester bond susceptible to cleavage by a cellular esterase.

25. A pharmaceutical composition comprising the isolated peptide of claim 1, in a pharmaceutically acceptable carrier.

26. A method of inhibiting replication of a human immunodeficiency virus in a cell, the method comprising contacting the cell with the peptide of claim 1 in a manner sufficient to inhibit replication of the capsid-containing virus in the cell.

27. The method of claim 26, wherein the cell is in a mammal infected with the human immunodeficiency virus.

28. The method of claim 27, wherein the mammal is a human.

29. The method of claim 27, further comprising treating the mammal with at least one additional anti-viral treatment.

30. A method of treating a mammal infected with a human immunodeficiency virus, the method comprising administering the pharmaceutical composition of claim 25 to the mammal in a manner sufficient to treat the mammal.

31. The method of claim 30, wherein the mammal is a human.

32. The method of claim 30, wherein the peptide is (SEQ ID NO: 6)

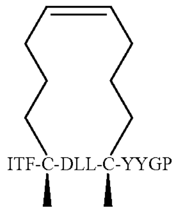

wherein the (C)s are the α-carbons of the unnatural amino acids.

33. The method of claim 30, wherein the mammal is a pregnant female.

34. The method of claim 30, further comprising treating the mammal with at least one additional anti-viral treatment.

* * * * *